US009816083B2

(12) United States Patent
Lin et al.

(10) Patent No.: US 9,816,083 B2
(45) Date of Patent: Nov. 14, 2017

(54) GENETICALLY ENGINEERED BACTERIUM FOR TREATMENT OF BREAST CANCER, METHOD FOR CONSTRUCTING THE BACTERIUM, AND APPLICATIONS THEREOF

(71) Applicant: NANJING SINOGEN BIOTECH & PHARMACEUTICAL INC., Nanjing, Jiangsu (CN)

(72) Inventors: Yan Lin, Jiangsu (CN); Sujin Zhou, Jiangsu (CN); Allan Zhao, Jiangsu (CN); Xiaoxi Li, Jiangsu (CN); Pengli Yu, Jiangsu (CN); Fanghong Li, Jiangsu (CN)

(73) Assignee: NANJING SINOGEN BIOTECH & PHARMACEUTICAL INC., Science Park, Jianning, Nanjing, Jiangsu (CN)

( * ) Notice: Subject to any disclaimer, the term of this patent is extended or adjusted under 35 U.S.C. 154(b) by 0 days.

(21) Appl. No.: 14/766,558

(22) PCT Filed: Feb. 27, 2014

(86) PCT No.: PCT/CN2014/072652
§ 371 (c)(1),
(2) Date: Aug. 7, 2015

(87) PCT Pub. No.: WO2014/131363
PCT Pub. Date: Sep. 4, 2014

(65) Prior Publication Data
US 2015/0376593 A1    Dec. 31, 2015

(30) Foreign Application Priority Data
Feb. 28, 2013 (CN) .......................... 2013 1 0062253

(51) Int. Cl.
| | | |
|---|---|---|
| A01N 63/00 | (2006.01) |
| C12N 9/88 | (2006.01) |
| C07K 14/195 | (2006.01) |
| C12N 15/74 | (2006.01) |
| A61K 38/00 | (2006.01) |
| A61K 48/00 | (2006.01) |

(52) U.S. Cl.
CPC ............... *C12N 9/88* (2013.01); *C07K 14/195* (2013.01); *C12N 15/74* (2013.01); *C12Y 404/01011* (2013.01); *A61K 38/00* (2013.01); *A61K 48/005* (2013.01)

(58) Field of Classification Search
CPC .......... C12Y 404/01011; C07K 14/195; C12N 15/74; C12N 9/88
See application file for complete search history.

(56) References Cited

FOREIGN PATENT DOCUMENTS

| CN | 1879890 | 12/2006 |
| CN | 101010002 | 8/2007 |
| CN | 103146626 | 6/2013 |

OTHER PUBLICATIONS

El-Sayed et al 2010, Applied Microbiol Biotechnol 86:445-467.*
Ganai et al 2009, British J. of Cancer 101:1683-1691.*
He, Q. et al., "Longitudinal Diffusion-Weighted MRI Study of the Tumor Tissue Destruction Process Induced by Novel Attenuated *Salmonella typhimurium* Expressing Protein Drugs", Proc. Intl. Soc. Mag. Reson. Med., vol. 15, Dec. 31, 2007.
Chen, Yingli et al., "Preliminary Study on Oral Attenuated Vaccine Carried Survivin-Δ3 (T34A) Gene and Its Antitumor Effect", Practical Preventive Medicine, ISSN 1006-3110, vol. 19, No. 1, Jan. 31, 2012.
International Search Report filed in PCT/CN2014/072652 dated May 28, 2014.
Talmadge, J.E., et al., Murine models to evaluate novel and conventional therapeutic strategies for cancer. American Journal of Pathology, 2007. 170(3): p. 793-804.
Voskoglou-Nomikos, T., et al., Clinical predictive value of the in vitro cell line, human xenograft, and mouse allograft preclinical cancer models. Clinical cancer research, 2003.9(11): p. 4227-4239.
Shoemaker, R.H., The NCI60 human tumour cell line anticancer drug screen. Nature Reviews Cancer, 2006. 6(10): p. 813-823.
De Jong, M. and T. Maina, Of Mice and Humans: Are They the Same?—Implications in Cancer Translational Research. Journal of Nuclear Medicine, 2010. 51(4): p. 501-504.
Sausville, E.A., et al., Contributions of human tumor xenografts to anticancer drug development. Cancer Res, 2006. 66(7): p. 3351-3354.
Johnson, J.I., et al., Relationships between drug activity in NCI preclinical in vitro and in vivo models and early clinical trials. Br J Cancer, 2001. 84(10): p. 1424.
Boulikas, T., et al., Recent clinical trials using cisplatin, carboplatin and their combination chemotherapy drugs (review). Oncol Rep, 2004. 11(3): p. 559-595.

(Continued)

*Primary Examiner* — Christopher M Babic
*Assistant Examiner* — Kelaginamane T Hiriyanna
(74) *Attorney, Agent, or Firm* — Jun He Law Offices P.C.; James J. Zhu

(57) ABSTRACT

The current invention discloses a genetically engineered bacterium used for the treatment of breast cancer. The said bacterium is attenuated *Salmonella typhimurium* VNP20009 with cloned L-methioninase gene. The method for constructing this genetically engineered bacterium and the application thereof are also disclosed herein. In the current invention, our biologic drug for the treatment of breast cancer is a type of safe, non-toxic new drug with anti-tumor activity. It can highly express methioninase through recombinant DNA technology using attenuated *Salmonella typhimurium* VNP20009 as a carrier, which has a strong anti-tumor activity and can meet the needs. The preparation method is simple and easy to operate, showing good application prospect.

4 Claims, 3 Drawing Sheets

(56) References Cited

OTHER PUBLICATIONS

Hoffman, R.M., Development of recombinant methioninase to target the general cancer-specific metabolic defect of methionine dependence: a 40-year odyssey. Expert Opin Biol Ther, 2015. 15(1): p. 21-31.

Toso, J.F., et al., Phase I study of the intravenous administration of attenuated *Salmonella typhimurium* to patients with metastatic melanoma. J Clin Oncol, 2002. 20(1): p. 142-52.

Heimann, D.M., et al., Continuous intravenous administration of live genetically modified *Salmonella typhimurium* in patients with metastatic melanoma. J Immunother, 2003. 26(2): p. 179-80.

\* cited by examiner

GENETICALLY ENGINEERED BACTERIUM FOR TREATMENT OF BREAST CANCER, METHOD FOR CONSTRUCTING THE BACTERIUM, AND APPLICATIONS THEREOF

TECHNICAL FIELD

The current invention relates to drugs for the treatment of cancers, in particular, to the construction and applications of the genetically engineered bacterium in preparing the drugs for the treatment of breast cancer.

BACKGROUND OF THE INVENTION

Breast cancer is one of the common malignancies of women, and its incidence is in the first place among female cancer patients. Currently the primary treatment procedures for breast cancer include surgery, radiotherapy, chemotherapy, and hormone therapy, etc. Chemotherapy is always playing an important role in the comprehensive treatment of breast cancer due to the sensitivity of breast cancer to anti-cancer drugs Traditional drugs for chemotherapy in breast cancer mainly include doxorubicin, cyclophosphamide, 5-fluorouracil, etc. Although these drugs have been widely used in the treatment of breast cancer, their therapeutic efficacy is limited due to the toxicity and resistance of patients. In recent years, targeted therapy is used clinically, with the primary drugs like Herceptin, tyrosine kinase inhibitor, lapatinib, pertuzumab monoclonal antibody, bevacizumab, flavopiridol, etc. However, due to patient's tolerance, physical properties of drugs like instability and solubility and the targets, targeted therapy only applies to a subgroup of patients. With the advances in bacterial- and viral-based gene therapy and genetic engineering technology, mounting studies have focused on bacterial treatment of tumors since the middle 1990s. Results have shown that *Salmonella typhimurium* can inhibit the growth of tumor cells in mice in a targeted and efficient manner.

*Salmonella* is a group of Gram-negative, invasive intracellular facultative anaerobes parasitized in human and animal intestinal tracts. VNP20009 is an attenuated *Salmonella typhimurium* strain with the deletion of msb B and pur I genes. It is genetically stable and sensitive to antibiotics. The msb B protein is necessary for the lipid acylation to endotoxin, and the lipid acylation at A-terminal cannot be achieved when deleted, lowering the toxicity. The pur I protein is involved in purine metabolism, deletion of this gene leads to dependence of exogenous adenine when culturing the bacteria. These gene manipulations in VNP20009 also lower the production of tumor necrosis factor (TNF), thereby reducing the inflammatory response. Consequently, the low pathogenicity improves the safety of its clinical usage. VNP20009 has been widely used in cancer research, which can influence the growth of a variety of solid tumor models of mice, including melanoma, lung cancer, colon cancer, breast cancer, renal cancer and prostate cancer. VNP20009, as a vector of gene therapy, has the ability to accumulate in the tumor site in a highly targeted fashion. Researchers have found in the mouse models carrying a variety of solid tumors that the quantity of VNP20009 in tumors is 200-1000 times as high as that in non-cancerous major organs, such as the liver. It uses a more complex set of mechanisms to target tumors. VNP20009 can preferentially accumulate and multiply under the hypoxic and necrotic conditions in the tumor tissue. At the same time, the bacteria multiply significantly faster in the tumor tissues than in the normal tissues, making it possible for the attenuated *Salmonella* to be a new type of anti-tumor agent and the vector of targeted gene therapy. Potential mechanisms for the effect of a slow tumor growth by VNP20009 may include the follows: 1) Breakdown of nutrients necessary for tumor growth by the bacteria, e.g., the enzymes produced by bacteria such as asparaginase, can deplete essential amino acids for tumor growth; 2) Stimulation of local toxin secretion or tumor necrosis factor α to tumor microenvironment can negatively influence the tumor angiogenesis. In addition, the non-specific inflammatory reaction at the bacterial growth site can activate anti-tumor T cells. Studies have shown that although attenuated *Salmonella* VNP2009 is an ideal carrier for gene therapy which can be applied safely with high allowable dose, its application independently has no strong anti-tumor effect and a further combination with other drugs is needed.

Tumor cells require adequate nutrition in order to maintain its high rate of reproduction. In addition to carbohydrates, the need for methionine (Met), glutamine, and arginine is particularly high. Previous studies have established that Met-dependency is a common feature of most tumor cells, such as breast cancer, lung cancer, colon cancer, kidney cancer, bladder cancer, melanoma, glioma, etc. High Met-dependency does not exist in normal cells. Both in vivo and in vitro experiments have confirmed that dietary intervention with methionine deficiency can delay the proliferation of tumor cells. However, long-term deficiency of Met can cause malnutrition, metabolic disorders, and aggravate tumor growth due to a long-term DNA hypomethylation. Thus, by specifically degrading Met to methylselenol, a-ketobutyrate and ammonia through L-methioninase and lowering the level of methionine in vivo, we will be able to effectively inhibit the growth of tumor cells or even degrade them. Experiments in animal models have confirmed that intraperitoneal injection of methioninase can inhibit the growth of Yoshida sarcoma and lung tumor in nude mice. In previous clinical trials, four patients with breast cancer, lung cancer, kidney cancer and lymphoma received methioninase injection once every 24 h. Methioninase could significantly reduce the methionine content in plasma. However, since methioninase is not natively expressed in mammalians, exogenous administration often causes the immunological response.

SUMMARY OF THE INVENTION

The first technical know-how in the current invention is to provide a genetically engineered bacterium for effective treatment of breast cancer. The strain is safe and non-toxic with anti-tumor activity and it can meet the clinical needs.

The second technical know-how in the current invention is to provide the method for constructing the above genetically engineered bacterium.

The final technical know-how in the current invention is to provide the application of the above genetically engineered bacterium.

To reach such goal, the current invention deployed the technical schemes as follows:

A genetically engineered bacterium for the treatment of breast cancer, and the said genetically engineered bacterium is attenuated *Salmonella typhimurium* VNP20009 with cloned L-methioninase gene.

Wherein the said VNP20009 contains pSVSPORT plasmid and the said L-methioninase gene is cloned on pSVSPORT plasmid.

The method for the construction of the genetically engineered bacterium for the treatment of breast cancer is as follows: the L-methioninase gene is subcloned into pUC57 plasmid, and then subcloned into pSVSPORT plasmid through Kpn I and Hind III restriction sites to obtain pSVSPORT-L-methioninase expression plasmid, which then is transformed into attenuated *Salmonella typhimurium* VNP20009, to obtain the genetically engineered bacterium.

Wherein the said electroporation condition is as follows: voltage 2400 V, resistor 400Ω, capacitor 25 µF, time constant 4 ms.

The application of above genetically engineered bacterium in preparing drugs for treatment of breast cancer.

The current invention provides a genetically engineered tumor-targeting bacterium. It has tumor targeting and can continuously express L-methioninase in tumor tissues, which then consume methionine and a series of other nutrients, and depletes the tumor cells of nutrition, causing slow growth. Besides, the strain possibly activates caspase-3 apoptosis signaling pathway, leading to the death of the host tumor cells. Therefore, it can be used as the drug for the treatment of breast cancer.

Beneficial effects: compared with prior technology, our drug used for the treatment of breast cancer is a new, safe, non-toxic biological drug with anti-tumor activity, which can highly express methioninase through recombinant DNA technology using attenuated *Salmonella typhimurium* VNP20009 as a carrier. It can meet the needs with a strong anti-tumor activity. The preparation method is simple and easy to operate, showing good application prospect.

DETAILED DESCRIPTION OF THE EMBODIMENT

The invention is described herein in connection with drawings and certain specific embodiments. However, to the extent that the following detailed description is specific to a particular embodiment or a particular use, this is intended to be illustrative only and is not to be construed as limiting the scope of the invention.

Example 1: Construction of Genetically Engineered Bacterium (1) Construction of Plasmids Expressing L-Methioninase Gene Firstly, the L-methioninase (GenBank: L43133.1) is synthesized and subcloned into pUC57 plasmid (GenScript Corporation), then subcloned into plasmid pSVSPORT (Invitrogen) through Kpn I and Hind III restriction sites, to get pSVSPORT-L-methioninase expressing plasmid. The specific procedures are as follows:

Double enzyme digestion of plasmid pSVSPORT with Kpn I and Hind III: 2 µg plasmid DNA, 3 µL 10× buffer, 1.5 µL Kpn I, 1.5 µL Hind III. Add ddH$_2$O to 30 µL and incubate at 37° C. for 3 h, and then separate the digests by 1% agarose gel electrophoresis, to cut out DNA bands with the size of 4.1 kb, and then purify DNA using the gel recovery and purification kit.

The DNA fragments in L-methioninase coding region obtained by gene synthesis are subcloned into plasmid pUC57 (GenScript Corporation). Perform restriction digests as follows: 3 µg plasmid DNA, 3 µL 10× buffer, 1.5 µL Kpn I, 1.5 µL Hind III. Add ddH$_2$O to 30 µL and incubate at 37° C. for 3 h. Then separate the digests by 1% agarose gel electrophoresis. We cut out DNA bands with the size of 1.2 kb, and then purify DNA using a gel recovery and purification kit.

The pSVSPORT (Kpn I/Hind III) is ligated to DNA fragment of L-methioninase coding region (Kpn I/Hind III). Add 2 µL vector, 6 µL inserted fragment, 1 µL T4 DNA ligase in the ligation reaction, and incubate at 16° C. for 16 h.

The ligation product is transformed to competent cells of *E. coli* DH5α (Takara). Use one tube 50 µL of DH5α competent cells and place on ice until thawing. Add 5 µL of the above ligation product to the DH5α and mix them gently, and then incubate on ice for 30 min; after heat shock at 42° C. for 60 s, cold shock on ice for 2 min; add 500 µL of LB without antibiotic and culture at 37° C. with shaking for 1 h; spin tube at 4000 rpm for 5 min; remove all but 100 µL of LB and resuspend pellet with pipette tip. Place suspensions on LB plate containing ampicillin, and then incubate at 37° C. for 16 h.

Figure 1:
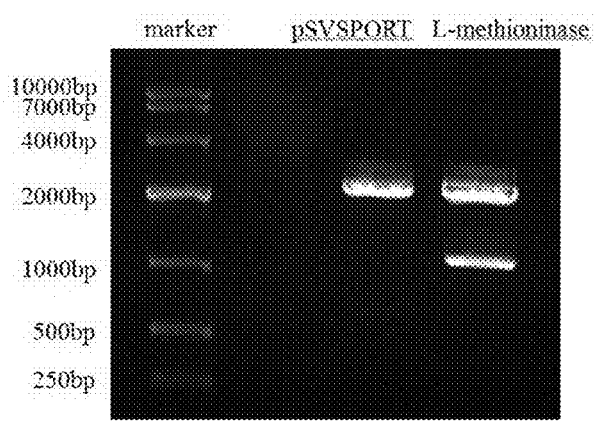
FIG. 1 shows 1% agarose gel electrophoresis by plasmid pSVSPORT-L-methioninase following restriction enzyme digestion.

When clones grow out, pick up the monoclonal colonies into 3 mL LB containing ampicillin, culture at 37° C. with shaking for 1 h. Extract the plasmid DNA from cultures and identify by Kpn I and Hind III restriction analysis. DNA bands of 4.1 and 1.2 kb are measured in positive clones, as shown in FIG. 1. Then the positive clone is sent for sequencing to confirm the identity of the insert fragment.

(2) Construct VNP20009-L-Methioninase Strain

The plasmid pSVSPORT and pSVSPORT-L-methioninase are electroporate into VNP20009 strain (YS1646), named VNP20009-V and VNP20009-M respectively. The specific construction procedures are as follows:

Place competent bacteria VNP20009 on ice. After thawing, transfer it to a pre-cooled electroporation cuvette and add 24 plasmid, slightly mix them, then incubate on ice for 1 min. Put the cuvette into electroporation apparatus seted to 2400 V, 400 Ω, 25 µF and 4 ms. After pulse, immediately add 1 mL SOC medium to the cuvette and mix gently. Culture at 37° C. with shaking for 1 h, centrifuge at 4000 rpm for 5 min and remove all but 100 µL of LB and resuspend pellet with pipette tip. Plate the electroporation mixture on LB plate containing ampicillin, and then incubate at 37° C. for 16 h. After VNP20009-V and VNP20009-M are cultured with LB, extract the plasmid and identification by restriction digestion.

Figure 2:
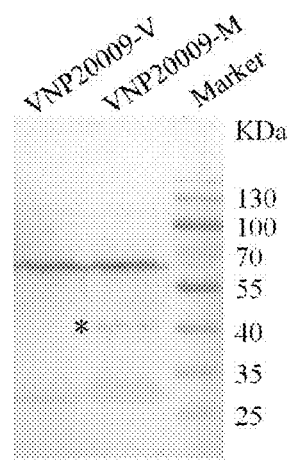
FIG. 2 shows methioninase expression identification by Western blot.

Extract proteins from 1×10$^8$ *Salmonella* and separate by 10% SDS-PAGE electrophoresis, transfer to PVDF membranes in an ice bath. The membranes are blocked by incubation in BSA at room temperature for 1 h. After three 5-min washes in TBST, the membranes are incubated at 4° C. overnight with rabbit antibody against L-methioninase (1:1000). After three 5-min washes in TBST, the membranes are incubated with horseradish peroxide-conjugated anti-rabbit secondary antibodies (1:10000) for 1 hr at room temperature. After three 5-min washes in TBST, the protein bands are visualized using enhanced chemiluminescence (ECL) reagents. The results are shown in FIG. 2. There is a specific band at about 43 kD molecular weight, suggesting compared with that of VNP20009 and VNP20009-V, L-methioninase expression of VNP20009-M is significantly increased.

Example 2: The Anti-Tumor Effect of VNP20009-L-Methioninase Strain

1. Culture breast cancer cell MDA-MB-231 using MEM medium containing 10% fetal bovine serum and inoculate $2 \times 10^6$ cells on the right armpit of nude mice. Observe the state of mice every 2 to 3 days and measure the tumor size using a vernier caliper (volume=$0.52 \times length \times width^2$). When the tumor size reaches 0.1~0.2 cm$^3$, tumor-bearing mice are randomized: PBS, VNP20009-V and VNP20009-M groups.

Figure 3:
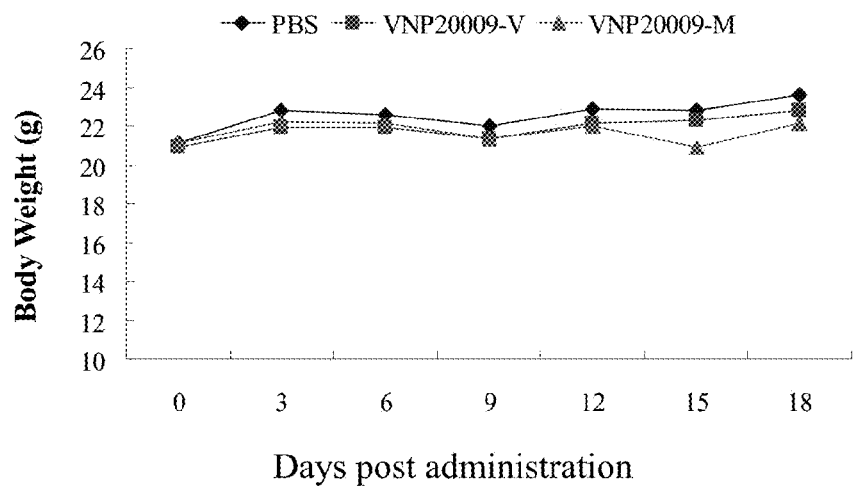
FIG. 3 shows the influence of *Salmonella* injection on the body weight of nude mice.

2. Culture VNP20009-V and VNP20009-M with LB-O. When OD≈0.6, collect the thallus and re-suspend it in PBS. Mice are administered by intratumoral injection at a dose of $2 \times 10^6$ CFU each, while the control group are administered with the same volume of PBS. After administration, observe the activities, eating Patterns and body weight of nude mice, results are shown in FIG. 3. After bacterial injection, the body weight of mice is not affected; moreover, the feeding and feces of nude mice have no abnormalities, indicating that VNP20009-V and VNP20009-M have no obvious toxicity to nude mice.

Figure 4:
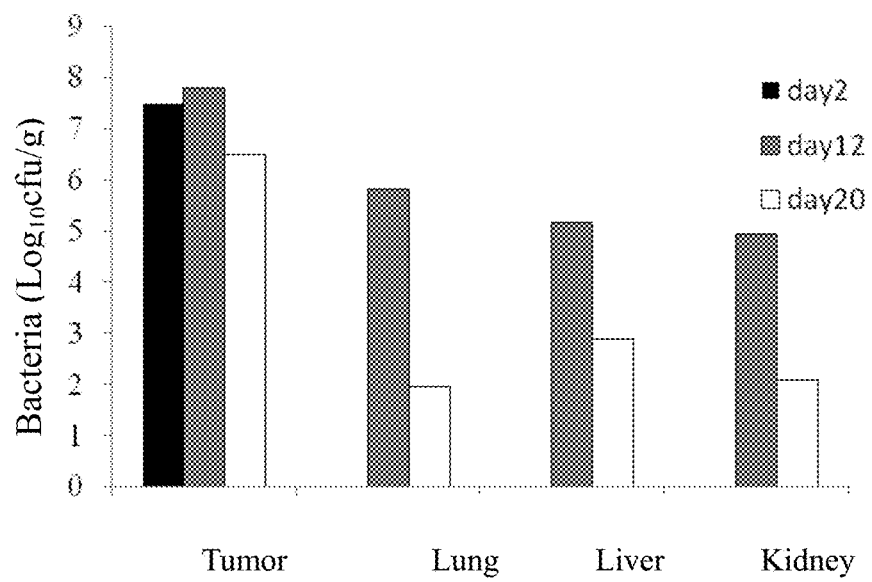
FIG. 4 shows the results of *Salmonella* distribution following intratumoral injection in nude mice.

3. After administration, on day 2, 12, 20, take major tissues of nude mice, to grind and homogenize with PBS and culture them on LB plates overnight after gradient dilution. Results are shown in FIG. 4—the quantitative colony count results of tissue homogenate. After two day of intratumoral bacteria injection, the bacteria count in the tumor tissue is $3 \times 10^7$ CFU/g, while no bacteria is detected in liver, kidney, etc. Twelve days later, the count of bacteria in the tumor tissue is $6.3 \times 10^7$ CFU/g, while that in the liver is $1.5 \times 10^5$ CFU/g, to reach a ratio about 400:1. Twenty days later, the ratio of bacteria between the tumor tissue and other tissues is about 4000:1~35000:1, indicating that VNP20009 has a well targeting ability to this kind of breast tumor.

Figure 5:
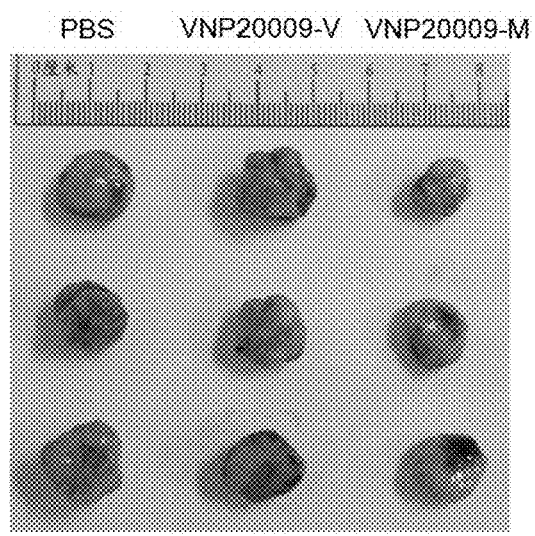
FIG. 5 shows the tumor size 2 weeks after administration of *Salmonella*.
Figure 6:
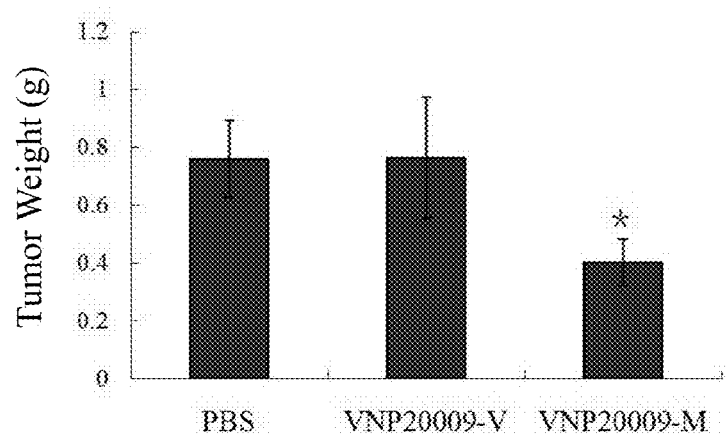
FIG. 6 shows the tumor weight 2 weeks after administration of *Salmonella*.

4. Measure the length and width of the tumor every 2-3 days, calculate the tumor volume and plot the tumor volume curve of nude mice. Two weeks after administration, there is a significant difference in the tumor size between the control and experiment group. Randomly take three mice from each group, strip the tumor of the nude mice, weigh it and take photos. The results are shown in FIG. 5 and FIG. 6, after administration of *Salmonella* VNP20009-M, the tumor grows slowly, the tumor volume and weight is about ½ of that in the PBS and VNP20009-V group, but there is no significant difference between VNP20009-V and PBS group, suggesting that VNP20009 with high expression of L-methioninase has significant inhibitory effect on the tumors of breast cancer.

Figure 7:
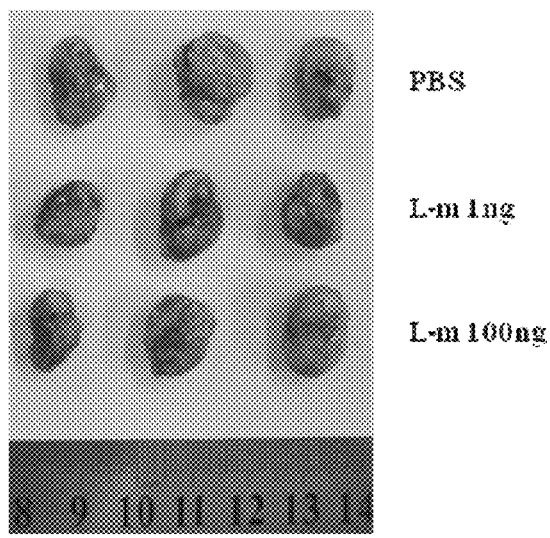
FIG. 7 shows the tumor size 2 weeks after administration of L-methioninase.
Figure 8:
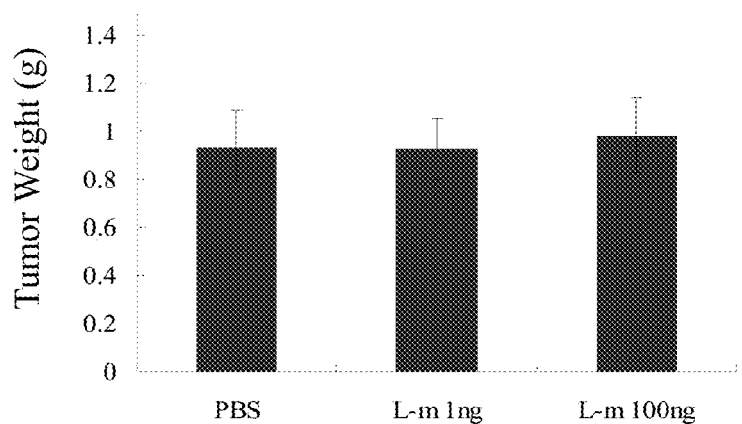
FIG. 8 shows the tumor weight 2 weeks after administration of L-methioninase.

5. The procedures are the same as those in 1. Tumor-bearing nude mice are divided into three groups and administered with PBS, L-methioninase 1 ng/mouse, L-methioninase 100 ng/mouse by intratumoral injection. Two weeks later, tumors are stripped, weighed and photographed. Results are shown in FIGS. 7,8. There is no significant difference in tumor size and weight among the three groups. The L-methioninase level in L-methioninase ing/mouse is equivalent to that contained in $2 \times 10^6$ CFU VNP20009-M. Thus, the administration of equal or even 100-fold dose of L-methioninase shows no significant anti-tumor effects. This indicates that with the L-methioninase depletion or degradation, a single administration does not function, while the continuous high-expression of L-methioninase using VNP20009 as the carrier can make up this drawback, showing significant anti-tumor effects.

The invention claimed is:

1. A method for treating human breast cancer, the method comprising administering a genetically engineered bacterium to a human having breast cancer, wherein the genetically engineered bacterium is attenuated *Salmonella typhimurium* VNP20009 comprising a cloned L-methioninase gene.

2. The method according to claim 1, wherein the L-methioninase gene is subcloned into pUC57 plasmid, and then subcloned into pSVSPORT plasmid through Kpn I and Hind III restriction sites to obtain pSVSPORT-L-methionase expression plasmid, which then is transformed via electroporation into attenuated *Salmonella syphimurium* VNP20009, to obtain the genetically engineered bacterium.

3. The method according to claim 2, wherein conditions for the electroporation are as follows: voltage 2400V, resistor 400Ω, capacitor 25 μF, time constant 4 ms.

4. The method according to claim 1, wherein the genetically engineered bacterium is included in drug preparation for the treatment of human breast cancer.

\* \* \* \* \*

UNITED STATES PATENT AND TRADEMARK OFFICE
CERTIFICATE OF CORRECTION

PATENT NO. : 9,816,083 B2
APPLICATION NO. : 14/766558
DATED : November 14, 2017
INVENTOR(S) : Lin et al.

It is certified that error appears in the above-identified patent and that said Letters Patent is hereby corrected as shown below:

On the Title Page

Item (72) Inventor Allan Zhao should be Allan Zijian Zhao.

Signed and Sealed this
Twenty-fourth Day of May, 2022

Katherine Kelly Vidal
*Director of the United States Patent and Trademark Office*